(12) United States Patent
Brouard et al.

(10) Patent No.: US 8,324,567 B2
(45) Date of Patent: Dec. 4, 2012

(54) ION SPECTRUM ANALYSING APPARATUS AND METHOD

(75) Inventors: Mark Brouard, Oxford (GB); Claire Vallance, Oxford (GB); Andrei Nomerotski, Oxford (GB)

(73) Assignee: University of Southampton, Southampton (GB)

( * ) Notice: Subject to any disclaimer, the term of this patent is extended or adjusted under 35 U.S.C. 154(b) by 218 days.

(21) Appl. No.: 12/747,321

(22) PCT Filed: Dec. 12, 2008

(86) PCT No.: PCT/GB2008/004085
§ 371 (c)(1),
(2), (4) Date: Aug. 4, 2010

(87) PCT Pub. No.: WO2009/074799
PCT Pub. Date: Jun. 18, 2009

(65) Prior Publication Data
US 2010/0294924 A1 Nov. 25, 2010

(30) Foreign Application Priority Data
Dec. 12, 2007 (GB) .................................. 0724295.1

(51) Int. Cl.
*H01J 49/40* (2006.01)
(52) U.S. Cl. .................. 250/287; 250/281; 250/282
(58) Field of Classification Search .................. 250/287, 250/286, 281, 282, 283
See application file for complete search history.

(56) References Cited

U.S. PATENT DOCUMENTS

| | | | | |
|---|---|---|---|---|
| 5,712,479 A | * | 1/1998 | Reilly et al. | 250/282 |
| 7,928,361 B1 | * | 4/2011 | Whitehouse et al. | 250/281 |
| 7,947,950 B2 | * | 5/2011 | Enke et al. | 250/290 |

FOREIGN PATENT DOCUMENTS

| | | |
|---|---|---|
| EP | 0290046 A3 | 11/1988 |
| GB | 2397940 A | 8/2004 |
| RU | 2143110 C1 | 12/1999 |

OTHER PUBLICATIONS

International Search Report for International Appln. No. PCT/GB2008/004085 (Dated Jan. 21, 2010).
UK Search Report for Appln. No. GB0624755.5 (Dated Apr. 7, 2007).
Martinez-Haya et al. "Photodissociation and multiphoton dissociative ionization processes in $CH_3S2CH_3$ at 193 nm studied using velocity-map imaging" Journal of Chemical Physics, vol. 120, No. 23, Jun. 15, 2004, pp. 11042-11052.
Wim G. Roeterdink and Maurice H. M. Janssen "Femtosecond velocity map imaging of dissociative ionization dynamics in $CF_3I$" Phys. Chem. Chem. Phys., vol. 4, Jan. 16, 2002, pp. 601-612.

(Continued)

*Primary Examiner* — Kiet T Nguyen
(74) *Attorney, Agent, or Firm* — Flaster/Greenberg, P.C.

(57) ABSTRACT

An ion spectrum analysing apparatus (1) comprising an electric field generation arrangement (3, 4, 5) which, in use, is operative to accelerate ions into a flight tube (7), and further comprising a detector (6), and recording apparatus (8) which is operative to record data representative of the spatial distribution of scattered ions impacting on the detector, and in use the recording apparatus is triggered at multiple times to record spatial distribution data relating to respective times-of-arrival of the ions.

30 Claims, 3 Drawing Sheets

OTHER PUBLICATIONS

Brouard et al. "Velocity-map imaging study of the $O(^3P)+N_2$ product channel following 193 nm photolysis of $N_2O$" Journal of Chemical Physics, vol. 119, No. 2, Jul. 8, 2003, pp. 771-780.

Bass M. J. et al. "Angular momentum alignment of $Cl(^2P_{3/2})$ in the 308 nm photolysis of $Cl_2$ determined using Fourier moment velocity-map imaging" Phys. Chem. Chem. Phys. vol. 5, Jan. 23, 2003, pp. 856-864.

Gebhardt Christoph R. et al. "Slice imaging: A new approach to ion imaging and velocity mapping" Review of Scientific Instruments, vol. 72, No. 10, Oct. 1, 2001, pp. 3848-3853.

Lin Jim J. et al. "Application of time-sliced ion velocity imaging to crossed molecular beam experiments" Review of Scientific Instruments, vol. 74, No. 4, Apr. 1, 2003, pp. 2495-2500.

Townsend Dave et al. "Direct current slice imaging" Review of Scientific Instruments, vol. 74, No. 4, Apr. 1, 2003, pp. 2530-2539.

Goji Ethod T et al. "An image sensor which captures 100 consecutive frames at 1,000,000 frames per second" IEEE Transactions on Electron Devices, vol. 50, No. 1, Jan. 1, 2003, pp. 144-151.

\* cited by examiner

ION SPECTRUM ANALYSING APPARATUS AND METHOD

FIELD OF THE INVENTION

The present invention relates generally to ion spectrum analysing apparatus and to a method of ion spectrum analysis. In particular, although not exclusively, the present invention relates to mass spectrometry.

SUMMARY OF THE INVENTION

According to a first aspect of the invention there is provided ion spectrum analysis apparatus comprising:
an electric field generation arrangement which in use is operative to accelerate ions into a flight tube,
a detector,
recording apparatus which is operative to record data representative of the spatial distribution of scattered ions impacting on the detector,
and in use the recording apparatus is triggered at multiple times to record spatial distribution data relating to respective times of arrival of the ions.

The data provided by the apparatus relating to an ion scattering distribution may preferably be used in a number of ways, either to obtain structural information on a parent molecule or dynamical information on the fragmentation process itself. For example, if fragmentation is induced by absorption of polarised light, the speed and angular scattering distribution of the fragments is likely to depend strongly on the conformation of the parent molecule. In a second example, the angular distributions of fragment ions arising from collisionally-induced fragmentation processes may reveal a great deal about the detailed mechanism of the fragmentation, which in turn yields structural information on the parent molecule. This type of information is impossible to obtain from a standard mass spectrum.

In one embodiment of the invention a mass spectrometer is arranged to operate in what may be termed a velocity-mapping mode. In the velocity mapping mode the velocity distribution (ie speed and angular distribution) of the ions at their point of formation is mapped onto a spatial distribution of the ions at the detector. When measured from the centre of the recorded image, each spatial position is proportional to the velocity component of the ion in the detector plane. Accordingly, the mass of each ionic species and the complete speed and angular distributions of each ionic species and correlations between them are obtained for a sample in a 'single shot'. The resulting scattering distributions recorded by the detector reflect details of the disassociation processes leading to ion formation on an event-by-event basis.

In another embodiment, the mass spectrometer is preferably of sufficiently high spatial and time resolution to carry out so-called coincidence measurements involving two or more particles and/or photons resulting from a photophysical and photochemical processes. Coincidence measurements involve detection of at least two different particles produced in the same event. Such measurements provide additional information as compared to detecting each particle separately, as they can identify physical, chemical and/or spatial correlations between the detected fragments. The mass spectrometer is advantageously capable of separating the fragments to be detected in time and/or space and of ensuring that a single set of fragments arrives at the detector per event (since if two sets of fragments from two different events arrive at the detector simultaneously then there will be no way of determining which fragments are correlated and the coincidence measurement will fail). A set of data resulting from a single coincidence measurement comprises arrival positions on the detector and respective arrival times of the fragments, and a large number of such measurements are used to build up a statistical picture of the probability distributions (e.g. angular scattering distributions, speed distributions and so on) associated with the process under study.

In another embodiment a mass spectrometer is arranged to operate in what may be termed a spatial mapping mode. When arranged to operate in a spatial imaging mode the electric field generation arrangement is tuned to map the spatial distribution of the ions at the source (ie at the point of their formation) to the spatial distribution on the detector. The recorded distribution is a two dimensional projection of the three dimensional spatial distribution. Accordingly a spatial imaging mode is particularly suitable for high throughput multi-sample surface imaging mass spectroscopy.

In one embodiment of the invention the recording apparatus, preferably comprising a fast pixel device with appropriate spatial and timing resolution, is used to record images for each mass simultaneously (for either velocity-map or spatial-map imaging). The device may comprise Charge Coupled Device (CCD) or Complimentary Metal Oxide Semiconductor (CMOS) technologies but is not limited to those. Multiple images are recorded over the timescale of the time-of-flight mass spectrum, spanning up to hundreds of microseconds, with a time resolution of tens of nanoseconds.

According to a second aspect of the invention there is provided a method of ion spectrum analysis comprising accelerating ions towards a detector and controlling recording apparatus to record the spatial distribution of scattered ions on the detector at each of various times of arrival at said detector.

BRIEF DESCRIPTION OF THE DRAWINGS

Various embodiments of the invention will now be described, by way of example only, with reference to the accompanying drawings in which.

DETAILED DESCRIPTION OF EXEMPLARY EMBODIMENTS OF THE INVENTION

Figure 1:
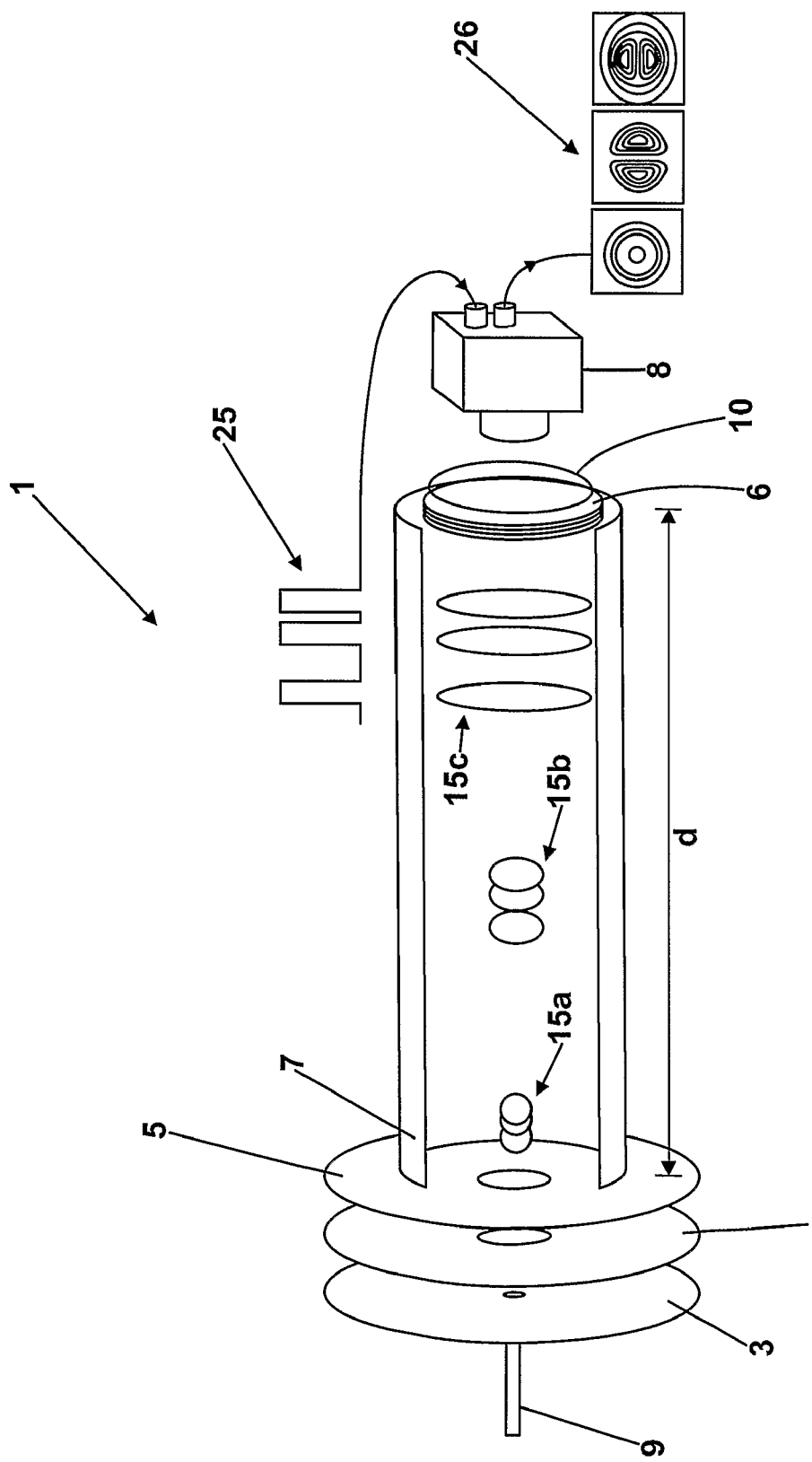
FIG. 1 is a schematic representation of a mass spectrometer apparatus.

With reference to FIG. 1 there is shown a mass spectrometer apparatus 1 which comprises an ionization source (not illustrated) coupled to a set of imaging ion lenses 3, 4 and 5, a position-sensitive detector 6, a flight tube 7 and a fast-framing CCD camera 8. Samples to be ionised are fed into the sample inlet 9. Virtually any standard ionization source used in conventional mass spectrometry experiments may be interfaced to the apparatus; for example, photoionization, electron impact, electrospray or matrix-assisted laser-desorption ionization (MALDI) should all be possible. In FIG. 1, ionization is achieved within the ion lens system 3, 4 and 5 through laser photoionization.

Mass selection within the apparatus is based on the known technique of time-of-flight mass spectrometry. Following ionization, the ions are accelerated through an electrostatic potential V provided by the ion optics 3, 4 and 5. The final velocities v of the ions are determined by their mass-to-charge ratios (m/q) according to the relationship $$v = \left(\frac{2qV}{m}\right)^{1/2}$$

The ions then travel through the flight tube 7 which is a field-free region, to the detector 6, with the time at which each ion strikes the detector being given by $$t = \frac{d}{v} = d\left(\frac{m}{2qV}\right)^{1/2}$$

where d is the length of the flight tube 7. The total ion current reaching the detector 6 as a function of time will therefore show a series of peaks, each corresponding to the arrival of a packet 15 of ions of a particular mass-to-charge ratio, the packets of respective ion species becoming gradually spaced apart as they progress through the tube 7 due to their different velocities. As seen in FIG. 1 the trajectories 15*a*, 15*b*, and 15*c* of three packets of ions are shown.

The assembly 6 comprises a pair of microchannel plates (MCPs) mounted in a chevron configuration and coupled to a phosphor screen 10. Each ion striking the front face of the MCPs elicits a cascade of electrons through one of the channels, and the pulse of electrons leaving the back face of the MCPs is accelerated towards the phosphor screen 10, producing a pulse of light. In this way the spatial distribution of ions striking the detector 6 is transformed into an image on the phosphor screen 10, which is recorded using the camera 8 which is appropriately time-gated (as will explained in more detail below) and transferred to data processing apparatus (such as a PC) for processing, storage, and later analysis.

When operating in a velocity map imaging mode, in addition to providing an acceleration potential to direct ions towards the detector, the potentials applied to the velocity-mapping lenses 3, 4 and 5 are carefully tuned such that: (i) all ions with the same velocity component in the plane of the two-dimensional position-sensitive detector 6 strike the detector at the same position relative to the time-of-flight axis; and (ii) the velocity distribution is focused along the time-of-flight axis such that the three-dimensional scattering distribution is compressed into a two-dimensional 'pancake' by the time the distribution reaches the detector 6. When these conditions are satisfied, the signal recorded at the detector 6 at a given time-of-flight comprises a two-dimensional representation of the full three-dimensional scattering distribution for ions of the corresponding chosen m/q. In other words in the velocity mapping mode the velocity distribution (ie speed and angular distribution) of the ions at their point of formation is mapped onto a spatial distribution of the ions at the detector. When measured from the centre of the recorded image each spatial position is proportional to the velocity component of the ion in the detector plane.

Figures 2, 3:
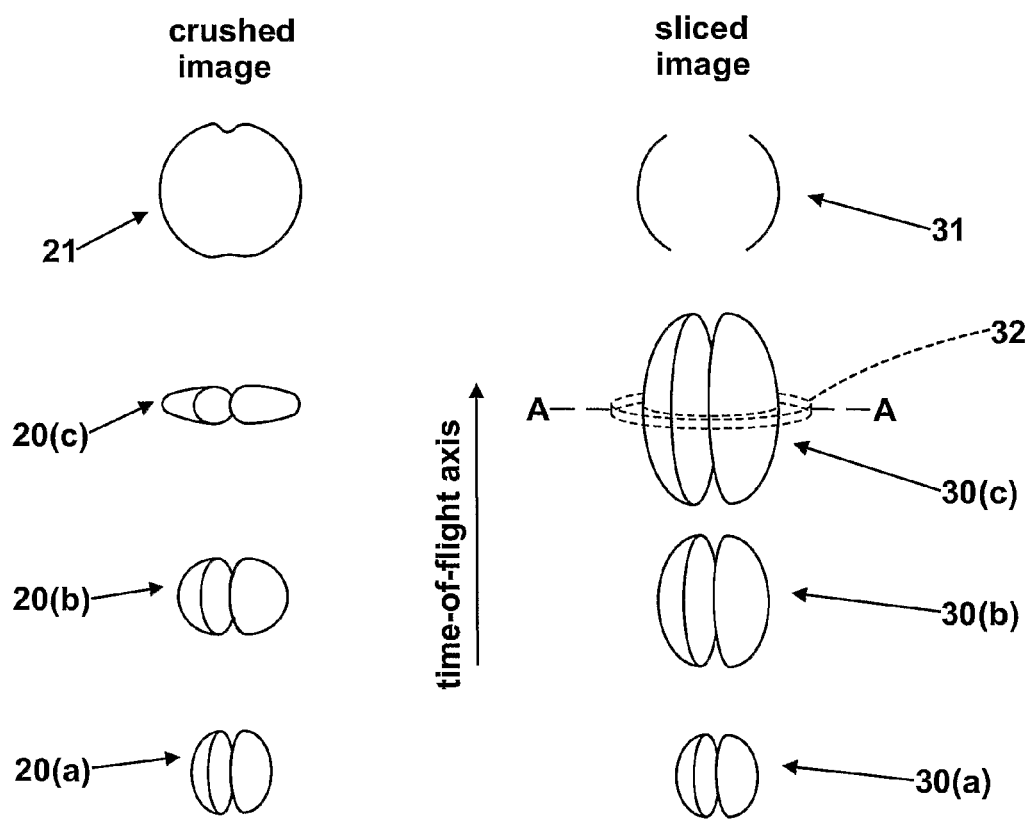
FIG. 2 is a schematic representation of the trajectory of a first ion fragment distribution.
FIG. 3 is a schematic representation of the trajectory of a second fragment distribution.

With reference to FIG. 2 various snapshots 20(*a*), 20(*b*) and 20(*c*) of a fragment distribution packet progressing along the flight tube 7 are shown. As is evident the ion optics 3, 4 and 5 are configured to provide a 'crushed' fragment distribution which impacts on the detector 6. When a molecule is dissociated using linearly polarised light, the velocity distribution of the fragments is cylindrically symmetric about the electric field vector of the dissociating light. Various mathematical techniques are available for reconstructing the full three-dimensional distribution of the fragments about the axis of the dissociation vector from the recorded image 21. For example, an Abel transform could be used to re-inflate the recorded two-dimensional pancake image into three dimensions.

A variant on the above technique of using 'crushed' fragment distributions may be termed 'slice imaging', in which the ion lenses 3, 4 and 5 are tuned to stretch the velocity distribution of each fragment distribution along the time-of-flight axis rather than compressing it. This stretching of the fragment distribution is shown in FIG. 3 in which the snapshots 30(*a*), 30(*b*) and 30(*c*) show how the lobes of the distribution gradually become increasingly elongated along the time-of-flight axis. This allows the camera 8 to be time-gated to a subset of ions of each mass. By sweeping the gate through the arrival-time profile for a given ion, the 3D velocity distribution may be measured directly as a sequence of 'slices'. The symmetry of the velocity distribution of a given fragment distribution often means however that all the information on the distribution is contained in a single central slice, as shown with reference numeral 32, so that only one slice need be recorded for each mass. The complete distribution about the dissociation vector axis A-A is reconstructed as the solid of revolution generated when the slice is rotated about the axis.

When arranged to operate in a spatial imaging mode the lenses 3, 4 and 5 are tuned to map to the spatial distribution of the ions at the source (ie at the point of their formation) to the spatial distribution on the detector. The recorded distribution is a two dimensional projection of the three dimensional spatial distribution. Accordingly a spatial imaging mode is particularly suitable for surface imaging since surfaces are inherently two dimensional.

Figure 4:
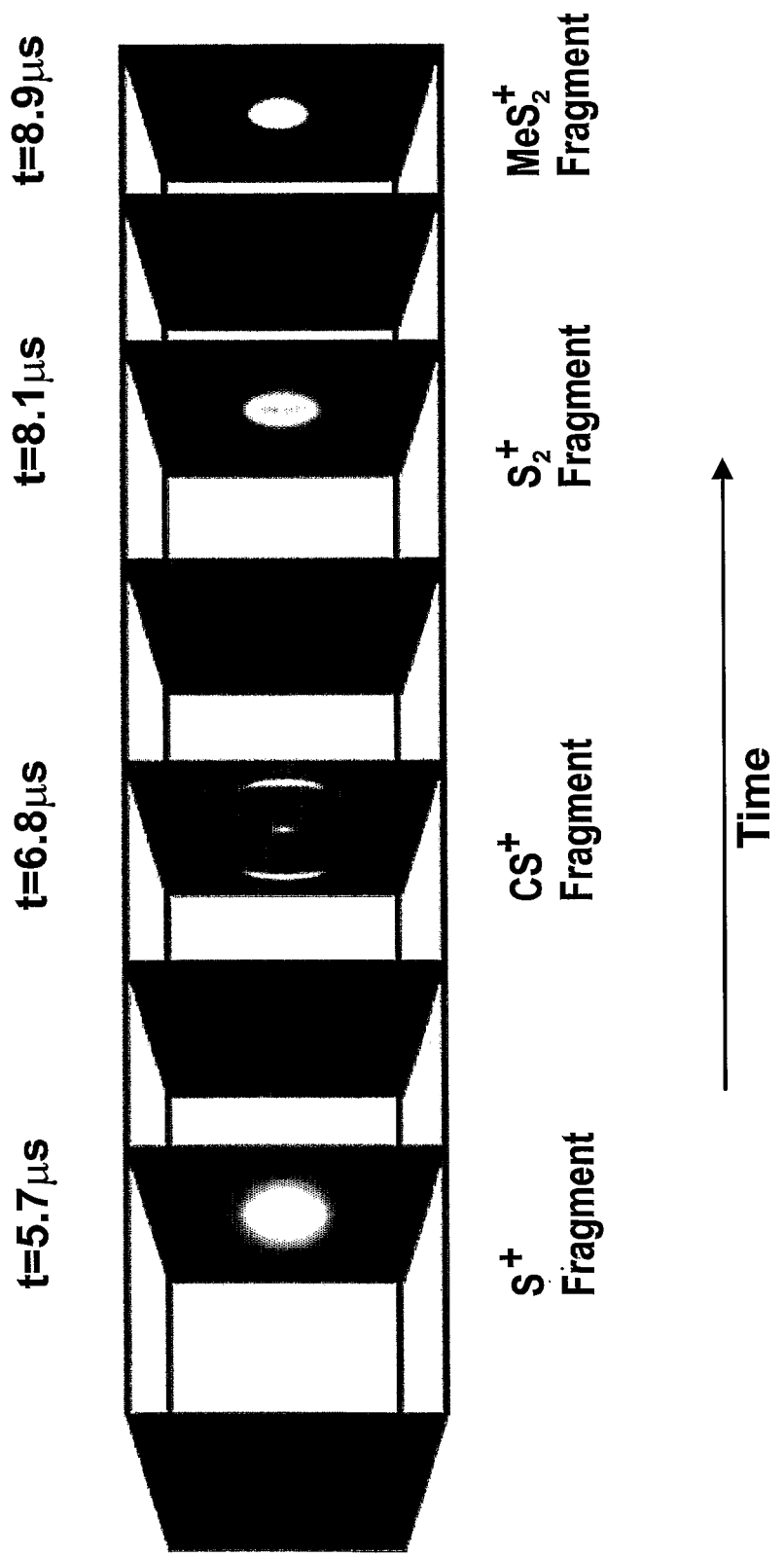
FIG. 4 is a schematic representation of recorded images of various fragment distributions.

In order to record images for each mass simultaneously (for either velocity-map or spatial-map imaging), the CCD camera is of the ultra-fast multiple-frame-transfer type. Multiple images need to be recorded on the timescale of microseconds over which a time-of-flight mass spectrum is recorded. In a multiple frame-transfer camera, each pixel incorporates a memory implemented in a CCD register, allowing multiple frames to be stored within the pixel during the data capture. When the camera 8 is triggered (or 'clocked'), the charge stored on the exposed photosensitive part of the pixel is transferred into the first cell of the CCD register, at the same time shifting the previously recorded cells by one. This charge transfer process in the registers occurs simultaneously across all of the pixels in the CCD chip. By synchronising the clocking of the CCD chip to the arrival of consecutive mass peaks at the detector, images for each mass peak may be stored on the chip, up to a maximum number of images determined by the number of memory cells in the register within each pixel. The exposure time for each frame and the time required to transfer charge between registers may be as short as a few nanoseconds. Once the desired number of images has been stored, the complete set of data may be read out at a much slower rate (of the order of milliseconds) to a PC for processing and storage As is shown schematically in FIG. 1 at 25 the camera 8 is triggered at three time intervals, each corresponding to the arrival of one of the ion packets. At 26 is shown schematic representations of the recorded images of the three ion packets. With reference to FIG. 4 there is shown the sequence of recorded images, and associated times-of-flight, of respective fragments resulting from multiphoton photolysis and ionization of dimethyldisulfide, $CH_3S_2CH_3$, at a wavelength of 193 nm, together with blank spacing images there between.

In an alternative embodiment to the above fast-framing CCD camera 8, apparatus for recording data at multiple times of arrival comprises a Complimentary Metal Oxide Semiconductor (CMOS) device. The CMOS device can function in the same fast framing mode as the above mentioned CCD camera or could provide more sophisticated processing at pixel level. For example, a time stamp and respective amplitude information could be assigned to each hit pixel in the detector. Data recorded by the CMOS device can be read out using the standard 'rolling shutter' method. In turn, the CMOS unit can be interfaced to a computer, similarly to the arrangement described above for CCD camera embodiment.

It will be appreciated that both the CCD and CMOS devices are sensitive to both visible light and to charged particles. When used in a light-detection mode, they provide a direct replacement for the conventional CCD camera used in the imaging mass spectrometer described above, recording light from the phosphor located behind the MCPs. In an alternative embodiment, their sensor region is used to detect the electrons emitted from the back face of the MCPs directly. Such an embodiment provides an optimal performance in terms of spatial and temporal resolution, since it eliminates the need for a phosphor, which can reduce the intrinsic resolution of the MCPs. In this embodiment, the MCPs are suitably configured, and an additional set of electrostatic lenses is used to map the image formed by the electrons leaving the back face of the MCPs onto the front face of the sensor region. The lens system is arranged to accelerate the electrons from the MCPs to a sufficiently high energy to allow them to penetrate a passive coating material the front of the sensor region.

Whilst map imaging mass spectrometry can be used in conjunction with laser ionization 9 (as described above), in principle velocity-map imaging mass spectrometry may be coupled to any of the standard types of ion source used in conventional mass spectrometry. This includes electron impact ionization, electrospray ionization, matrix-assisted laser-desorption ionization (MALDI) and photoionization using either a laser or a synchrotron source. This flexibility makes it a highly versatile technique with a wide range of applications in many fields of mass spectrometry. A few possible applications are given below.

(i) Detailed dynamical studies on fragmentation processes in small molecules, induced either by photon absorption or electron impact.

(ii) Discovery of previously hidden pathways that lead to the same set of ionic fragments. This in turn could help to identify chiral components and help to optimise their production.

(iii) The technique may provide a useful alternative to ion mobility techniques and H/D exchange for obtaining conformational information on larger molecules through the conformation-dependence of fragment-ion velocity distributions. Fragmentation patterns would be different for denatured and for native (folded) proteins. This could provide an alternative to the known ion mobility methods that are used for obtaining conformational information on gas phase biomolecules. Ion mobility (IMS) has been used for conducting such studies. One could conduct a two stage experiment in which conformations are selected using IMS and then fragmented and imaged to obtain an imaging mass spectrum of different isolated conformers. For example, a velocity-map imaging arrangement could be used as the second stage in a tandem mass spectrometer.

(iv) Mass spectrometry is widely used in peptide and oligonucleotide sequencing. In these applications, the sample is fragmented within the spectrometer and the fragment masses analysed to determine the sequence of amino acids or nucleotides. Measuring the fragment velocity distributions along with their masses should aid the data analysis by allowing similarities in the velocity distributions for pairs of co-fragments to be exploited.

(v) There is currently considerable interest in imaging of the MALDI plume in order to improve understanding of the ion formation mechanism. This is usually achieved through laser-induced fluorescence of dye-tagged sample molecules, which simply indicates the positions of the tagged species a chosen time after the MALDI laser pulse. Velocity-map imaging mass spectrometry could be used to image all species present simultaneously, and measuring fragment velocities directly should provide further insight into the energetics of the MALDI process.

(vi) There is an existing technique known as 'imaging mass spectrometry' in which a series of standard mass spectra of ions formed through MALDI at different positions within a solid sample are recorded. The peak intensities at each point are then used to build up a map of the spatial variation in the concentrations of various atomic or molecular species of interest within the sample. The technique is finding increasing applications in the characterisation of biological tissue samples. By tuning the ion optics in our imaging spectrometer to space-focus rather than velocity-focus the ions, and by illuminating a larger area (as opposed to illumination using a tightly focused beam) of the surface with the laser beam in the desorption/ionization step, it should be possible to measure MALDI-type images for each ion of interest directly in a single step. The camera 8 would be triggered at the respective time-of-arrival of the ions of interest. This method may be described as spatial profiling of specific atomic or molecular species in or on a surface. This would provide large gains in efficiency over the existing method of scanning the laser, recording a conventional mass spectrum at each point and using the set of recorded spectra to generate an image, and would also largely eliminate any effects of experimental drift during the data acquisition sequence. Advantageously such a 'single shot' MALDI imaging would provide an increased data acquisition rate. Furthermore since the data is obtained in a single shot there is no issue about damage to the surface from a previous shot (as in a rastering arrangement).

(vii) Multi-sample mass spectrometry is possible in which an array or 'grid' of different samples are initially subjected to spatial mapping of the surfaces of all of the samples. This would simultaneously provide the full ion spectrum for each sample. Advantageously, obtaining such mass-resolved images of multiple samples reduces data collection times significantly. In a subsequent step, the ion optics could then be tuned to concentrate on a sample of interest and to provide velocity mapping for that sample. The velocity mapping would then provide, for example, detailed information on the fragmentation process. Alternatively/in addition the second or a subsequent step may comprise performing a (further) spatial imaging of the sample of interest but at a higher resolution.

(viii) The apparatus 1 is designed primarily for use in place of a standard mass spectrometer in order to characterise the velocity and angular distributions of ionic fragments in addition to their mass. In principle however, it could be used in place of a standard mass spectrometer for virtually any experiment, limited only by the available number of image registers on the CCD or CMOS chip.

(ix) It will be appreciated that a conventional time-of-flight mass spectrum may be measured in coincidence with the images by recording the total ion current striking the channel plate detector, or the total electron current striking the screen. Alternatively a beamsplitter may be used to divert some of the light from the phosphor to a photomultiplier tube.

(x) With some modifications to the electrostatic potentials applied to the ion lenses 3, 4 and 5, the apparatus 1 could also be used for an imaging version of photoelectron spectroscopy (PES). Photoelectron spectroscopy is widely used for characterising solid surfaces, and is also applied to gas-phase species. The technique involves time-of-flight measurements of electrons emitted from a sample following irradiation by a pulse of fixed-wavelength high-energy laser radiation. When a sample molecule absorbs a photon, some of the photon energy is used to ionise an electron from the molecule, with the balance being released into kinetic energy of the electron. As a result, electrons with different binding energies, emitted from different molecular orbitals within the sample, have characteristic velocities, and give rise to a series of well-defined peaks in a time-of-flight measurement. Standard PES measurements, which measure the total electron current reaching the detector as a function of time, therefore reveal the energy-level structure of the sample molecule. However, the angular distribution of the electrons, as measured in an imaging experiment, provides additional information on the detailed spatial structure of the molecular orbitals from which the electrons are emitted. Photoelectron imaging is a possible use of velocity-map ion imaging. However, current techniques allow images of only one electron peak at a time to be obtained. The multiplexing provided by the inventive apparatus 1 would allow angular distributions for all of the electron peaks of interest to be measured simultaneously.

The invention claimed is:

1. An ion spectrum analysing apparatus comprising:
an electric field generation arrangement which in use is operative to accelerate ions into a flight tube,
a detector, recording apparatus which is operative to record data representative of the spatial distribution of scattered ions impacting on the detector, and
wherein in use the recording apparatus is triggered at multiple times over a single time-of-flight mass spectrum to record spatial distribution data relating to respective times-of-arrival of the ions.

2. The apparatus as claimed in claim 1 wherein the recording apparatus is arranged to be triggered at times relating to the times-of-arrival of different ionic species.

3. The apparatus as claimed in claim 1 the electric field generation arrangement is configured to distribute a group of the ions substantially transversely of the longitudinal axis of the flight tube.

4. The apparatus as claimed in claim 1 wherein the electric field generation arrangement is configured to distribute a group of the ions substantially along the longitudinal axis of the flight tube.

5. The apparatus as claimed in claim 4 wherein the recording apparatus is arranged to record the spatial distribution of ions impacting on the detector in a median region of the group, the region being substantially transverse to the longitudinal axis of the flight tube and being substantially central of the envelope of the group.

6. The apparatus as claimed in claim 5, further comprising data processing apparatus, the data processing apparatus being configured to process the recorded spatial distribution data so as to provide data indicative of a three dimensional representation of the velocity distribution at the time of formation, and wherein an Abel transform methodology is used by the data processing apparatus to determine the three dimensional velocity distribution of the ions in the group using the recorded data relating to the median region.

7. The apparatus as claimed in claim 1 wherein the electric field generation arrangement is configured to cause the recorded spatial distribution data to be substantially representative of mapping data of the velocity distribution of the ions at the time of formation.

8. The apparatus as claimed in claim 7 further comprising data processing apparatus, the data processing apparatus being configured to process the recorded spatial distribution data so as to provide data indicative of a three dimensional representation of the velocity distribution at the time of formation.

9. The apparatus as claimed in claim 1 wherein the electric field generation arrangement is arranged to cause the ions to reach the detector such that the recorded spatial distribution data can be used to determine the position or positions of the ions at the time of formation.

10. The apparatus as claimed in claim 9 wherein the electric field generation arrangement is arranged to cause ions to reach the detector such that the recorded spatial distribution data can be used to determine the position or positions of the ions in or on a sample under investigation.

11. The apparatus as claimed in claim 1 wherein the recording apparatus comprises a camera.

12. The apparatus as claimed in claim 11 wherein the camera comprises a Charged Coupled Device (CCD) assembly of a multiple-frame-transfer type.

13. The apparatus as claimed in claim 1 wherein the recording apparatus comprises a Complimentary Metal Oxide Semiconductor (CMOS) device.

14. The apparatus as claimed in claim 1 wherein the detector comprises a position-sensitive detection arrangement.

15. The apparatus as claimed in claim 14 wherein the detector comprises a microchannel plate assembly.

16. The apparatus as claimed in claim 14 wherein the detector further comprises a phosphorescent screen assembly.

17. A method of ion spectrum analysis comprising the steps of:
accelerating ions towards a detector and
controlling a recording apparatus to record the spatial distribution of scattered ions on the detector at each of various times-of-arrival at said detector over a single time-of-flight mass spectrum.

18. The method as claimed in claim 17 further comprising the step of triggering the recording apparatus at times relating to the times-of-arrival of different ionic species.

19. The method as claimed in claim 18 further comprising the step of using an electric field generating means to distribute a group of the ions substantially transversely of the longitudinal axis of the flight tube.

20. The method as claimed in claim 19 wherein the electric field generating means is arranged to distribute a group of the ions substantially along the longitudinal axis of the flight tube.

21. A method of mass spectroscopy as claimed in claim 18.

22. The method as claimed in claim 17 wherein the recording apparatus comprises a camera apparatus and wherein the camera apparatus is used to record images of the spatial distribution of successive groups of ions impacting on a detector.

23. The method as claimed in claim 17 further comprising the steps of
arranging the spatial distribution of the ions on reaching the detector to be substantially representative of mapping data, and
determining the velocity distribution of the ions at the time of formation as a function of the mapping data.

24. The method as claimed in claim 17 further comprising the step of arranging the spatial distribution of the ions on reaching the detector to be substantially representative of a position or positions of the ions at the time of formation.

25. The method as claimed in claim 24 wherein data indicative of position of the ions in a sample region is obtained as a first step and as a subsequent step the velocity distribution of ions in a particular sub-region is obtained.

26. The method as claimed in claim 17 wherein the ions are generated by way of photoionization.

27. The method as claimed in claim 17 wherein the ions are generated by way of electrospray ionization.

28. The method as claimed in claim 17 wherein the ions are generated by way of matrix-assisted laser-desorption ionization.

29. A method of photoelectron spectroscopy as claimed in claim 17.

30. A method of determining a sequence of amino acids or nucleotides as claimed in claim 17.

* * * * *

UNITED STATES PATENT AND TRADEMARK OFFICE
CERTIFICATE OF CORRECTION

PATENT NO.         : 8,324,567 B2
APPLICATION NO.    : 12/747321
DATED              : December 4, 2012
INVENTOR(S)        : Mark Brouard, Claire Vallance and Andrei Nomerotski Page 1 of 1

It is certified that error appears in the above-identified patent and that said Letters Patent is hereby corrected as shown below:

On the Title Page, Item (73) under the Assignee section, change the Assignee Name to read as follows:

Isis Innovation Limited,
Summertown, Oxford (GB)

Signed and Sealed this
Second Day of April, 2013

Teresa Stanek Rea
*Acting Director of the United States Patent and Trademark Office*